(12) United States Patent
Erazo-Majewicz et al.

(10) Patent No.: US 8,790,627 B2
(45) Date of Patent: Jul. 29, 2014

(54) PERSONAL CARE COMPOSITION ADDITIVE FOR APPLICATION ON KERATIN SUBSTRATES TO PROVIDE LONG LASTING BENEFITS

(75) Inventors: Paquita Erazo-Majewicz, Landenberg, PA (US); Gijsbert Kroon, Giessendam (NL); Thi Hong Lan Le-Pham, Voorburg (NL); Tuttu Maria Nuutinen, Delft (NL)

(73) Assignee: Hercules Incorporated, Wilmington, DE (US)

(*) Notice: Subject to any disclaimer, the term of this patent is extended or adjusted under 35 U.S.C. 154(b) by 161 days.

(21) Appl. No.: 13/168,390

(22) Filed: Jun. 24, 2011

(65) Prior Publication Data

US 2011/0318285 A1    Dec. 29, 2011

Related U.S. Application Data

(60) Provisional application No. 61/358,226, filed on Jun. 24, 2010.

(51) Int. Cl.
| | | |
|---|---|---|
| *A61Q 5/12* | (2006.01) | |
| *A61Q 5/00* | (2006.01) | |
| *A61Q 19/00* | (2006.01) | |
| *A61Q 5/02* | (2006.01) | |
| *A61K 8/73* | (2006.01) | |
| *A61K 8/34* | (2006.01) | |
| *A61K 8/81* | (2006.01) | |

(52) U.S. Cl.
CPC .. *A61Q 5/12* (2013.01); *A61Q 5/02* (2013.01); *A61K 8/737* (2013.01); *A61K 8/345* (2013.01); *A61Q 5/004* (2013.01); *A61K 8/8158* (2013.01); *A61K 8/731* (2013.01); *A61K 2800/5426* (2013.01); *A61K 8/817* (2013.01)
USPC ............... 424/70.13; 424/78.02; 424/401

(58) Field of Classification Search
None
See application file for complete search history.

(56) References Cited

U.S. PATENT DOCUMENTS

| | | | |
|---|---|---|---|
| 6,582,711 B1 * | 6/2003 | Asmus et al. | 424/405 |
| 2006/0182703 A1 * | 8/2006 | Arisz et al. | 424/70.13 |
| 2007/0202067 A1 * | 8/2007 | Kolly-Hernandez et al. | 424/70.11 |

OTHER PUBLICATIONS

Tara E Gottschalck; Gerald N McEwen 1-26 (Editors): "International Cosmetic Ingredient Dictionary and Handbook, CTFA 13th Ed", Jan. 1, 2810 (Jan. 1, 2010), Personal Care Products Council, Washington, XP002676467, ISBN: 1-882621-47-6, pp. 4583,4656,4696,5479,4897,5489,5628,5633.
International Search Report, PCT/US2011/041820, May 24, 2012, p. 1.

* cited by examiner

*Primary Examiner* — Jyothsna Venkat
(74) *Attorney, Agent, or Firm* — Shaorong Chen

(57) ABSTRACT

The present invention relates to a personal care composition additive for use on keratin substrates in order to provide long lasting benefits to the keratin substrate such as in conditioning systems, such as 2/1 shampoo's, leave-on and rinse off conditioners, for hair and skin, or for imparting greater water resistance to such personal care compositions as sunscreens or cosmetics.

19 Claims, 5 Drawing Sheets

PERSONAL CARE COMPOSITION ADDITIVE FOR APPLICATION ON KERATIN SUBSTRATES TO PROVIDE LONG LASTING BENEFITS

RELATED APPLICATIONS

This application claims the benefit of Provisional Application 61/358,226 filed on Jun. 24, 2010, which is incorporated by reference in its entirety.

FIELD OF INVENTION

The present invention relates to a personal care composition additive for use on keratin substrates in order to provide long lasting benefits to the keratin substrate such as in conditioning systems for hair and skin. Conditioning systems typically used are 2/1 shampoo's, leave-on and rinse off conditioners. For repair of damaged hair, while conditioners do a better job than shampoos, they use eco-harmful cationic and amphoteric surfactants in conjunction with silicones, like amodimethicones. These systems provide good detangling properties and hydrophobicity to damaged hair, but these properties are lost after shampooing the hair. Permanent and semi-permanent hair colors are used with similar type of conditioners, which show poor color lasting performance upon washing with cleansing systems. The present invention relates to personal care composition additive which permits the majority of the substantive surfactants found in conditioning systems to be replaced by specific compositions of substantive polymers. The personal care composition additives of this invention provide detangling properties; easy combability and color-lasting through multiple wash cycles with shampoo after the treatment.

BACKGROUND OF THE INVENTION

To modify the properties of hair and skin to improve their condition or state of being, consumers use a wide variety of personal care products. These products comprise various surfactants and chemical additives collectively referred to as conditioners or conditioning agents. Examples of personal care products include hair care products, skin care products, deodorants, antiperspirants, lotions, creams and others.

For personal care products, there is growing demand from consumers to have products designed specifically for conditioning their distinctive hair or skin. A particular challenge is to condition hair damaged by heat, mechanically or chemically through bleaching or coloring the hair. Consumers desire to have such a product for providing both initial conditioning of their hair and maintaining the hair conditioning upon multiple treatments with shampoo or other cleansing systems. Another need in the industry is to move to more environment friendly systems by reducing the aquatoxicity and skin irritancy. Hair colors, permanent and semi-permanent, show color fading upon washing with shampoos or rinsing with water. That is another need the industry would like to see resolved.

Current conditioning systems for damaged hair use one or more combinations of cationic surfactants, amphoteric surfactants, silicones, fatty alcohols, polyquaterniums, amino acids, proteins, lipids and humectants. Wet conditioning of damaged hair is accomplished by neutralizing the anionic charge of the hair by positively charged surfactants and polymer and creating a hydrophobic layer from surfactant and polymers. This creates a reduction of the swelling of the hair fibers by making it more hydrophobic and reducing friction of the fibers, overall resulting in detangling, manageability and soft feel of the hair. Upon treatment with cleansing systems like shampoo's, 2/1 shampoo's, body washes or shower gels, the combing performance, detangling properties, hydrophobicity of the hair and lubricity are not maintained sufficiently, while colored hair loses the strength of the color upon washing.

SUMMARY OF THE INVENTION

The present invention relates to a personal care composition additive for providing prolonged benefit to a keratin surface. The personal care composition additive is composed of a substantive polymer, and a water miscible, polar solvent. The solution of the substantive polymer and the water miscible, polar solvent is at a concentration of substantive polymer to solvent in the range of about 0.1 wt % to about 20 wt %, and the substantive polymer has a molecular weight (Mw), as determined by size exclusion chromatography, in the range of greater than about 50 kDalton to less than or equal to about 800 kDalton. The substantive polymer has a cationic degree of substitution (Cat-DS) of greater than about 0.001 units, and the substantive polymer is selected from the group consisting of polysaccharides and synthetic polymers containing cationic monomers.

The present invention also relates to personal care compositions comprising the personal care composition for providing prolonged benefit to a keratin surface and a personal care active ingredient.

BRIEF DESCRIPTION OF THE FIGURES

Further embodiments of the present invention can be understood with the appended figures.

DETAILED DESCRIPTION OF THE INVENTION

Figure 1:
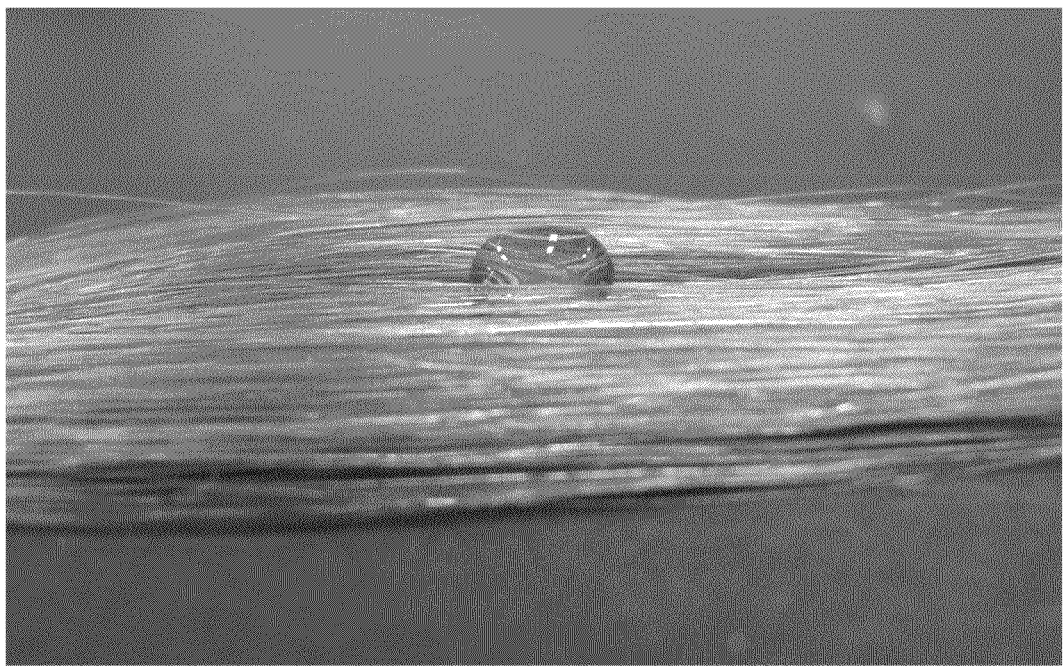
FIG. 1 is a photograph of a water droplet on the surface of a bleached Caucasian hair tress treated with the personal care composition additive of the present invention demonstrating the hydrophobicity imparted to the hair tress by the personal care composition additive.

The present invention relates to a personal care composition additive which is composed of a combination of substantive conditioning polymers, preferably based on a cellulosic or galactomannan backbone, delivered as a polymer solution or in combination with a fatty alcohol. This personal care composition additive shows excellent conditioning performance as leave-on and, especially, as rinse-off conditioner. The substantive conditioning polymers are cationic polysaccharides based on hydroxyethyl cellulose or galactomanan and show improved conditioning performance over nonionic polymers, proteins and quaternized proteins. Alternatively, the substantive conditioning polymers may be synthetic polymers containing cationic monomers. A preferred synthetic polymer containing cationic monomers of use in the present invention is polydiallyldimethylammonium chloride (Poly-DADMAC).

The cationic polysaccharide of use in the present invention may be hydrophobically modified. It has been found that the more hydrophobic cationic polysaccharides, like cationic hydrophobically modified hydroxyethyl cellulose and cationic hydrophobically modified guar derivatives, demonstrate superior performance in solution when the personal care composition additive is used directly as a conditioner. The personal care composition additive of the present invention when incorporated into a personal care composition provides lasting performance. Where the personal care composition is a hair care composition, the benefits which may be extended using the personal care composition additive include conditioning, detangling, hydrophobicity and color lasting after multiple washes with cleansing systems like shampoos, conditioning shampoos shower gels, etc. Where the personal care composition is a skin care composition, the benefits which may be extended using the personal care composition additive include, moisturizing, hydrophobicity or waterproofing, UVA and/or UVB protection. An additional attribute of the personal care composition additive of the present invention is that it allows simplification of conditioner formulations and provides a reduced ecotox approach to conditioning by providing the personal care manufacturer with the opportunity to formulate conditioners without, or with reduced, silicones and cationic or amphoteric surfactants.

In the formation of a personal care composition, the personal care composition additive is combined with a personal care active ingredient to provide a benefit to the user's body. Personal care compositions include hair care, skincare and sun care products. Examples of substances that may suitably be included, but not limited to, in the personal care products according to the present invention are as follows: perfumes, which give rise to an olfactory response in the form of a fragrance and deodorant perfumes which in addition to providing a fragrance response can also reduce body malodor; skin coolants, such as menthol, menthyl acetate, menthyl pyrrolidone carboxylate N-ethyl-p-menthane-3-carboxamide and other derivatives of menthol, which give rise to a tactile response in the form of a cooling sensation on the skin; emollients, such as isopropylmyristate, silicone materials, mineral oils and vegetable oils which give rise to a tactile response in the form of an increase in skin lubricity; deodorants, as well as precursors to deodorants, other than perfumes, whose function is to reduce the level of or eliminate micro flora at the skin surface, especially those responsible for the development of body malodor; antiperspirant actives, whose function is to reduce or eliminate the appearance of perspiration at the skin surface; moisturizing agents, that keeps the skin moist by either adding moisture or preventing from evaporating from the skin; sunscreen active ingredients, which protect the skin and hair from UV and other harmful light rays from the sun; and hair treatment agents, that conditions the hair, cleans the hair, detangles hair, acts as styling agent, volumizing and gloss agents, anti-dandruff agent, hair growth promoters, hair dyes and pigments, hair perfumes, hair relaxer, hair bleaching agent, hair moisturizer, hair oil treatment agent, and antifrizzing agent.

For the cationic polysaccharides, like guar and cellulose derivatives, the cationic degree of substitution is related to its maximum number of hydroxyl groups, which is a maximum of 3 for e.g., cellulose derivatives.

The substantive polymer of use in the personal care composition additive has a cationic degree of substitution (Cat-DS) of greater than about 0.001 units. Preferably, the substantive polymer has a cationic degree of substitution in the range of 0.001 to about 3.0., preferably in the range of from about 0.2 to about 3.0, more preferably in the range of about 0.4 to about 3.0.

Cationic substitution of the polysaccharide is typically accomplished through the reaction of the polysaccharide hydroxyl groups with cationic epoxide reagents, where the cationic group is a quaternary ammonium group, or reaction of the hydroxyl groups with cationic reagents containing other reactive functionality, such as chlorohydrin functionality, or isocyanate functionality In order to analytically determine the amount of cationic substitution present in a cationic polysaccharide the following procedure is used:

Procedure for Determining the Amount of Cationic Substitution

Approximately 25 mg of sample is dissolved in 1.5 gm of 2M TFA. The solution vial was heated to 100° C. for 5 hours in a hot plate. The vial is cooled and then approximately 0.2 gm of $D_2SO_4$ is added and the solution is returned to the hot plate for one (1) more hour @100° C. Proton quantitative NMR is acquired using Bruker Avance II 400 MHz spectrometer.

Traditional conditioning products, like rinse off and leave on products contain a formulation chassis of cationic/amphoteric surfactants (e.g. benetrimonium chloride, cetrimonium chloride, stearamidopropyl dimethyl amine etc. . . . ) in combination with fatty alcohol (e.g. cetyl alcohol, cetearylalcohol), stearyl alcohol). In addition to this chassis, the formulations typically contain active ingredients like silicones (e.g. amodimethicone, dimethicone), oils, and proteins (hydrolyzed proteins, quaternized proteins, etc. . . . ). These traditional conditioning products do not provide prolonged benefits to keratin surfaces upon washing with cleansing products like shampoos.

It has been surprisingly found that polymer solutions with relatively low concentrations (<10 wt %), based on polymers with different degree of substantivity and aqueous solubility (hydrophobicity), can provide prolonged benefits to keratin surfaces in terms of conditioning or color after washing with a cleansing product like shampoo. The the concentration of the substantive polymer in the water miscible, polar solvent may be preferably about 1.0 wt %.

The polymer solutions on their own can provide these benefits, without the need to add cationic surfactants, amphoteric surfactants, fatty alcohols, silicones, proteins, etc. . . . The use of the polymer solutions for conditioning treatment does require the use of the correct solvent, considering the polymer structure and its solubility.

A polymer with high degree of cationic functionality, like hydroxyl propyl trimonium chloride modified HEC (Cat-DS ~0.45, Molecular weight approx. 200 kDalton), is soluble in water, but, as a 1% polymer solution, it does not provide the prolonged conditioning benefit. However, when applied in as a 1% polymer solution in water/glycerine (50/50), it does provide the conditioning upon multiple shampoo washes.

On the other hand, low charged hydrophobically-modified hydryoxyethylcellulose (HMHEC) (Cat-DS ~0.1, Mw approx. 220 kDalton) does provide the benefit when applied as an aqueous solution onto bleached hair.

Low-charged water soluble polymers; with preferably with some degree of hydrophobic modification, do provide this behaviour in diluted polymer solutions with concentration in the order of 1 wt %. Polymers with high cationic charge and polymers with reduced water solubility as a result of hydrophobic modification do provide this benefit in water/solvent mixtures or even from a more apolar solvent. The majority of those polymers when used as a personal care composition additive can be applied onto hair in the form of a polymer solution in a mixed aqueous solvent where water comprises a portion of the mixed aqueous solvent, and the other solvent being glycerine, polyethylene glycol, propylene glycol and other polar solvents. The molecular weight of the polymer of use in personal care composition additive of the present invention needs to be in a certain range of molecular weight (Mw), with extremely low (<50 k Dalton) or high molecular weight (Mw) polymers (800 kDalton) not providing the required substantive conditioning polymers properties, such as detangling.

Typical concentration of polymer in solutions as the personal care composition additive are around 1 wt %, which can be adjusted from 0.1 wt % up to 10 wt % depending on the viscosity of a final solution. The personal care composition additive is applied to hair in a range of 0.01-0.5 gram of polymer solution as an additive per gram of hair. This is similar to the application of conditioners, which can be leave on (typical application dosage <0.2 gram per gram hair) or rinse off (typical application dosage 0.1 gram/gram of hair). The polymer solutions can be prepared by diluting its solution with water and co-solvent in the case the polymer is already available in the form of a solution. In the case of a powder the polymer solution is prepared by sifting the polymer slowly to the vortex of water/solvent mixture or solvent.

The solvents of use in the personal care composition additive are water miscible, polar solvents. The solvent of use in the personal care composition additive is preferably an organo/water binary mixture where the organo component is preferably a water miscible polar solvent. The polar solvent in the mixture may be in the range of about 10:90 to about 90:10 by weight with water, preferably in the range of about 25:75 to about 75:25 by weight with water, more preferably about 50:50 by weight with water.

The water miscible polar solvent may be an alcohol, preferably a sugar alcohol, cyclitol, polyol or glycol ether. The polyols of use in the personal care composition additive may be selected from the group consisting of cyclitol, diols, glycerol, Balsaminol B, butanetriol, balsaminapentaol, cucurbalsaminol, and propylene glycol. Other solvents of use in the personal care composition additive are hydrogenated starch hydrolysdate, hydroxyl terminated polybutadiene, ioxilan, miglitol, 3-methoxy-4hydroxyphenylglycol, triethanol amine, trimethylolpropane, trimethyloethane, pentaerithritol or enterodiol.

Among the glycol ethers of use in the personal care composition additive are glycol ethers selected from the group consisting of diethylene glycol dimethyl ether, diethylene glycol monobutyl ether acetate, diethylene glycol monobutyl ether, diethylene glycol monoethyl ether acetate, diethylene glycol monoethyl ether, diethylene glycol monohexyl ether, diethylene glycol monomethyl ether acetate, diethylene glycol monomethyl ether, ethylene glycol dibutyl ether, ethylene glycol diethyl ether, ethylene glycol dimethyl ether, ethylene glycol monoacetate, ethylene glycol monobutyl ether acetate, ethylene glycol monoethyl ether acetate, ethylene glycol monoethyl ether, ethylene glycol monohexyl ether, ethylene glycol monomethyl ether acetate, ethylene glycol monomethyl ether, ethylene glycol monooctyl ether, ethylene glycol monophenyl ether, ethylene glycol monopropyl ether, triethylene glycol, triethylene glycol dimethyl ether, triethylene glycol monoethyl ether and triethylene glycol monomethyl ether.

The examples are presented to illustrate the invention, parts and percentages being by weight, unless otherwise indicated.

EXAMPLES

As benchmarks two commercial rinse off conditioners and two commercial leave on conditioners were tested as applied (leave on) or applied and rinsed off (rinse off products) and after washing with a simplified shampoo formulation (12 wt % Sodium lauryl ether (2EO) sulfate, 2 wt % cocamidopropyl betaine). The products were applied as 0.1 gram leave on conditioner per gram of hair or 0.3 gram of rinse off conditioner per gram of hair. The hair used was damaged by treating virgin brown hair by bleaching for 1 hour. This hair was used for all further testing. The shampoo was applied as 0.3 gram per gram of hair and then rinsed.

TABLE 1

| Example | | Wet comb energy (gf-mm) | Wet comb energy (gf-mm) after 3x shampoo wash |
|---|---|---|---|
| 1a (Comp.) | L'OREAL Elvive ™ anti-hair fracture conditioner rinse | 1464 | 311145 (after 1x shampoo) |
| 1b (Comp.) | Dove Therapy Intense ™ care conditioner rinse | 1252 | 110436 (after 1x shampoo) |
| 1c (Comp.) | KMS Silk sheen Spray leave on | 1662 | 25154 (1x shampoo) |
| 1d (Comp.) | L'OREAL Elvive ™ anti-hair fracture spray leave on | 1073 | 17944 |

The combing measurement was done on a texture analyzer without manually precombing the hair. From the Table above, it is evident that the commercial products formulated with cationic surfactants, proteins, fatty alcohol, silicones etc., show great conditioning after application, but after 3 shampoo rinses the products lose their conditioning performance completely. Comparative Examples 1a, 1b and 1c lose the performance after 1 rinse cycle. Comparative Example 1b was repeated by washing the hair with the Dove therapy 2/1 shampoo. The comb energy after 1× shampoo wash was 35211 gf-mm, showing that the recommended combination of the commercial conditioner with the commercial shampoo show some improvement, but not adequately.

As another benchmark, a simplified formulation with following composition was tested:

TABLE 2

| Example 2 (Comp.) | Wt % |
|---|---|
| Cetrimonium chloride | 0.5 |
| Behentrimonium chloride | 0.5 |
| Cetearyl alcohol | 3.0 |
| Water | 96.0 |

Formulation of comparative example 2 was applied at 0.3 grams per gram of hair and tested as rinse off conditioner and then after rinsing with a simple shampoo formulation (12 wt % Sodium lauryl ether sulfate –2 EO, 2 wt % Cocamidopropylbetaine). The comb energy was measured again. The results in Table 3 clearly demonstrate that the base formulation follows the same trend as the commercial products with poor conditioning (high comb energy) after multiple shampoo washes:

TABLE 3

|  | Wet comb energy (gf-mm) - rinse off | Wet comb energy (gf-mm) after 1x shampoo wash | Wet comb energy (gf-mm) after 2x shampoo wash |
| --- | --- | --- | --- |
| Formulation Example 2 (Comp.) | 1487 | 16507 | 21110 |

For testing a wide range of substantive polymers, simple solutions of the substantive polymers in 50% water/glycerine were used to screen the performance of the polymers. The glycerine was selected as part of the solvent system in order to solubilize more hydrophobic and water insoluble polymers. One example of the invention used to demonstrate that the water-glycerine solution behaved similar to a polymer-fatty alcohol mixture in water.

The polymer used in example 4 is a cationic hydrophobically modified hydroxyethyl cellulose with molecular weight of approx. 260 kDalton, Cationic degree of substitution of 0.30 and a cetyl modification of 1.7 wt %.

TABLE 4

| Example | Formulation | Wet comb energy (gf-mm) after rinse with water | Wet comb energy (gf-mm) after 1x rinse with shampoo | Wet comb energy (gf-mm) after 3x rinse with shampoo |
| --- | --- | --- | --- | --- |
| 4a | 1 wt % polymer, 3 wt % Cetearyl alcohol, 96 wt % water | 2650 | 3299 | 7868 |
| 4b | 1 wt % polymer, 49.5 wt % water, 49.5 wt % glycerine | 2385 | 2402 | 5285 |

The polymers hydroxyethyl cellulose derivatives (HEC) with hydrohobe (HM) and or cationic modification like hydropropytrimonium chloride (HPTM), commercially available as Quat™ 188 reagent (Dow Chemical Company) were used to make the polymer solutions of the present invention.

Polymers 5a thru 5 c are made through a process delivering non-uniformly substituted polymer backbone as described in patent publication US 20060182703A1, the disclosure of which is incorporated by reference in its entirety. The unsubstituted trimer ratio (U3R) is >0.21 with a HE-MS >1.3.

The molar substitutions (HE-MS) are in the range of 1.5-4.0:

TABLE 5

| Example | description | Mw (kDalton) | Hydrophobe type and wt % | Cationic type, DS (—) | Structure |
| --- | --- | --- | --- | --- | --- |
| 5a (Comp.) | Cationic HMHEC | 260 | Cetyl, 1.85 wt % | HPTM, 0.074 | Blocky |
| 5b (Comp.) | Cationic HMHEC | 1260 | Cetyl, 3.21 wt % | HPTM, 0.063 | Blocky |
| 5c (Comp.) | HMHEC | 260 | Cetyl, 1.93 wt % | None | Blocky |
| 5d | Cationic HMHEC | 220 | Cetyl, 1.50 wt % | HPTM, 0.09 | regular |
| 5e (Comp.) | HMHEC | 220 | Cetyl, 1.36 wt % | None | regular |
| 5f (Comp.) | HMHEC | 1260 | Cetyl, 2.20 wt % | None | regular |
| 5g (Comp.) | Cationic HEC | ~200 | none | HPTM, ~0.2 | regular |
| 5h | Cationic HEC | ~200 | none | HPTM, ~0.4 | regular |
| 5i (Comp.) | Cationic HEC | ~800 | none | HPTM, ~0.2 | regular |
| 5j (Comp.) | Polyquaternium 67 | ~800 | Not separate from the charge | HPTM + DiMethyl Dodecyl Trimonium, 0.25 | regular |
| 5k | Cationic HMHEC | ~300 | Lauryl 1.02 | HPTM 0.31 | Regular |
| 5l | Cationic HMHEC | ~300 | Lauryl 2.24 | HPTM 0.29 | Regular |
| 5m | Cationic HMHEC | ~300 | Butyl 1.7 | HPTM 0.29 | Regular |
| 5n | Cationic HMHEC | ~300 | Butyl 3.8 | HPTM 0.27 | Regular |
| 5o | Cationic HMHEC | ~300 | Cetyl 1.7 | HPTM 0.32 | Regular |

The polymers were tested as a 1 wt % solution in 50% water/50% glycerine. The polymer solutions were applied as a conditioner on damaged hair (0.3 g polymer solution per gram of bleached hair (1 hour bleached) and wet comb energies were measured after rinse with water 1, 3 and 5 times of shampoo wash (shampoo: 12/2 SLES/CAPB). The test results are provided in table 6.

TABLE 6

| Example | Wet comb energy (gf-mm) after rinse with water | Wet comb energy (gf-mm) after 1x rinse with shampoo | Wet comb energy (gf-mm) after 3x rinse with shampoo | Wet comb energy (gf-mm) after 5x rinse with shampoo |
|---|---|---|---|---|
| 5a (Comp.) | 2027 | 11760 | Too high to measure | |
| 5b (Comp.) | 55720 | Too high to measure | | |
| 5c (Comp.) | 73336 | Too high to measure | | |
| 5d | 1526 | 8304 | 12142 | 54006 |
| 5e (Comp.) | 18319 | 126650 | Too high to measure | |
| 5f (Comp.) | 115143 | 226873 | Too high to measure | |
| 5g (Comp.) | 14539 | 123356 | Too high to measure | |
| 5h | 4099 | 6244 | 9144 | 16461 |
| 5i (Comp.) | 7892 | 45678 | 112354 | Too high to measure |
| 5j (Comp.) | 5789 | 28812 | 78655 | Too high to measure |
| 5k | 4078 | 5593 | 11462 | 31396 |
| 5l | 1520 | 2758 | 4217 | 4972 |
| 5m | 1356 | 2179 | 4651 | 7463 |
| 5n | 3843 | 5482 | 9720 | 14287 |
| 5o | 2650 | 3299 | 7868 | 11897 |

From the above Table 6, it was shown that for adequate shampoo persistence, the cationic HEC derivatives perform at low Cat-DS (e.g. example 5d) when there was a hydrophobic modification present on the chain and molecular weight was reasonably low (<1 MM Dalton). For straight (non-hydrophobically modified) cationic HEC, the polymer functions at low molecular weight and high charge density (example 5h). With hydrophobic modification, even after 5 washes, the conditioning remained (e.g. example 5l, 5m, 5n and 5o).

The polymers of example 5d and 5o were tested in the formulation with 3% Cetearyl alcohol and 1 wt % polymers versus the system with 0.5 wt cetrimonium chloride and 0.5 wt % bentrimonium chloride.

The importance of polymer composition and solvent mixture was also demonstrated.

Example 5h is a cationic HEC with cationic DS of 0.45, Mw~220 kDalton. Example 5h as a polymer solution in water did not perform well after 1x shampoo wash where its wet comb energy was determined to be 65349 gf-mm. However, when the polymer of example 5h is applied as a 1% solution in water/glycerine solvent after 1x and 3x shampoo washes, the wet comb energy was measured as 6244 gf-mm and 9144 respectively, without manual precombing of the hair tresses.

The results are shown in Table 7 and are in agreement with the results for the polymer solutions. Example 5o demonstrates similar performance after 5 shampoo washes versus the reference system after 1 wash.

TABLE 7

| Example | Wet comb energy (gf-mm) after rinse with water | Wet comb energy (gf-mm) after 1x rinse with shampoo | Wet comb energy (gf-mm) after 3x rinse with shampoo | Wet comb energy (gf-mm) after 5x rinse with shampoo |
|---|---|---|---|---|
| Cetrimonium/ behentrimonium chloride | 1487 | 16507 | 110430 | Too high to measure |
| 5d | 4474 | 6632 | 14933 | 32373 |
| 5o | 2385 | 2402 | 5255 | 17592 |

TABLE 8

| Example | description | Mw (kDalton) | Hydrophobe type and wt %/DS | Cationic type, DS (—) |
|---|---|---|---|---|
| 6a | Cationic ethylguar | <50 | Ethyl, E-DS: 2.46 | HPTM, 0.13 |
| 6b | Cationic guar | 500 | none | HPTM, 0.13 |
| 6c | Butyl quat guar | 500 | Not separate | Butyl dimethyl ammonium: 0.2 |
| 6d | Cationic butyl guar | 500 | Butyl, 5 wt % | HPTM, 0.5 |
| 6e | Cationic HPGuar | 500 | HP: 0.2 | HPTM, 0.5 |

TABLE 9

| Example | Wet comb energy (gf-mm) after rinse with water | Wet comb energy (gf-mm) after 1x rinse with shampoo | Wet comb energy (gf-mm) after 3x rinse with shampoo | Wet comb energy (gf-mm) after 5x rinse with shampoo |
|---|---|---|---|---|
| 6a | 92552 | 380836 | | |
| 6b | 10256 | 15928 | | |
| 6c | 9194 | 18336 | | |

From the above results, it was evident that a substantive polymer with too low an Mw (see example 6a) does not provide adequate performance. It is preferred that the molecular weight of the substantive polymer is >50,000 Dalton.

In Table 8, commercial benchmarks like water, lauryldimonium Hydroxypropyl hydrolyzed wheat protein (Hydrotriticum QL, available from Croda Inc.) and amodimethicone were compared with the polymer of Example 5o in a formulation of 1 wt % polymer 3wt % cetearyl alcohol. In order to deliver sufficient viscosity 1 wt % of Natrosol® Plus 330 hydroxyethylcellulose (available from Hercules Incorporated) was added.

TABLE 10

| Example | Wet comb energy (gf-mm) after rinse with water | Wet comb energy (gf-mm) after 1x rinse with shampoo | Wet comb energy (gf-mm) after 3x rinse with shampoo | Wet comb energy (gf-mm) after 5x rinse with shampoo |
|---|---|---|---|---|
| 5o | 2495 | 3800 | | 8655 |
| Hydrotriticum QL | 120829 | 198178 | Too high to measure | |
| Amodimethicone | 31975 | 17562 | | |
| Acrylamido propyltrimonium chloride copolymer | 29236 | | | |
| polyquaternium 6 | 18297 | | | |

The example polymer 5o provided substantially better initial conditioning and rinse off performance than the quaternized protein and amodimethicone. The polymer of example 5o showed wash persistence at least up to 5 shampoo washes.

Two other polymers, acrylamidopropyltrimonium chloride copolymer (NHance® SP100 conditioning polymer, available from Hercules Incorporated) and polyquaternium 6 (PQ6) (Mw 850,000) were tested against the polymer of example 5o in a 50/50 water/glycerine solution. After rinse off, both the polymers showed too high a wet comb energy: 29236 gf-mm for SP100 and 18297 gfmm for PQ6.

Example 7

A 40% aqueous solution of polydadmac (example 7a) with a molecular weight of approximately 112,000 Dalton yielded better initial wet combing performance (5888 gf-mm), as well as better performance after multiple shampoo washes (3245 gf-mm after 5 washes), than the higher molecular weight (Mw 850,000) polyquaternium 6 comparative example referred above in Table 10, when applied at a 1 wt % concentration in combination with 3% ceteraryl alcohol.

Example 8

The results demonstrate for washing with a harsh cleansing system SLES/CAPB.

The shampoo was composed of 12 wt % SLES (2EO), 2 wt % CAPB, 0.2 wt % NHance CG13, 0.2 wt % carbomer (980 type), 2.5 wt % silicone (1.5 wt % active, 2.5% DC 1785). The formulation used for example polymer 5o was 1% polymer and 3% fatty alcohol.

TABLE 11

| Example | Wet comb energy (gf-mm) after rinse with water | Wet comb energy (gf-mm) after 1x rinse with shampoo | Wet comb energy (gf-mm) after 3x rinse with shampoo |
|---|---|---|---|
| 5o - SLES/CAPB | 1859 | 2285 | 7078 |
| 5o - 2/1 shampoo | 2385 | 2402 | 5255 |

Example 9

Dosage Level Shampoo, Conditioner

The dosage used was 0.3 gram conditioner per gram of hair and the same level for shampoo washes. In the Table below, the use levels were varied and it was observed that by reducing the conditioner level and increasing shampoo levels, the performance was negatively impacted, but the overall performance benefit was observed with example 5o:

TABLE 12

| Example | Conditioner (1% polymer, 3% FA) gram/ gram hair | Shampoo (SLES/CAPB 12/2) gram/ gram hair | Wet comb energy (gf-mm) after 1x rinse with shampoo | Wet comb energy (gf-mm) after 3x rinse with shampoo |
|---|---|---|---|---|
| 5o | 0.3 | 0.3 | 2402 | 5255 |
| 5o | 0.05 | 0.3 | 6140 | 11169 |
| 5o | 0.3 | 0.1 | 2649 | 4714 |

Example 10

For example 5d and example 7a, we compared the substantive polymers of the present invention in a system with cetearyl alcohol at 50% replacement by a cationic surfactant, stearamidopropyl dimethylamine in the system with 3% fatty alcohol. The washing was done with SLES/CAPB.

TABLE 13

| Example | Wet comb energy (gf-mm) after 1x rinse with shampoo | Wet comb energy (gf-mm) after 3x rinse with shampoo |
|---|---|---|
| 1% surfactant only | 89480 | 108984 |
| 5d-1% polymer | 13010 | 34891 |
| 5d-0.5% polymer, 0.5% surfactant | 15503 | 40812 |
| 7a-1% polymer + 1% surfactant | 2695 | 2012 |

From the Table above, it was evident that the replacement of polymer by 50% of cationic surfactant, had a negative impact of wash persistence for the conditioning polymers 5d, 5o and 7a. However, it was also shown that more hydrophobe (example 5o vs. 5d) and higher charge (7a vs. 5d, 5o) provided good results even at 50% replacement or maintaining all surfactant in for polymer 7a. All the polymers still showed wash persistence better than the surfactant base system without polymer.

Example 11

The wash persistence of the conditioning systems containing the polymers of the invention is also of value for preventing color fading in hair colors. Hair tresses (3x) were treated with a red color known for its fading issue. The hair color used was a permanent color from Henkel Schwarzkopf: Syoss Professional Performance Permanent Coloration Mahonie Acajou. The process used was as follows:
Open the application bottle with developing cream, add color from the tube, close bottle and shake until homogeneous mixture Start the dying process immediately onto dry hair tresses by massaging down the length of the tress during 1 minute
Cover the hair with aluminum foil and wait 30-45 minutes
Rinse off with water (35 C) by massaging the hair until the water is completely clear
Wash with mild silicone free shampoo
Use a BYK-Gardner Spectrophotometer to measure the changes in color indexes (L*a*b)
Total hair color ΔL (+lighter)
Red-green Δa (+redder, −greener)
Yellow-blue (+yellower, −bluer)
Total difference $\Delta E = [(\Delta L)^2 + (\Delta a)^2 + (\Delta b)^2]^{1/2}$
Place tress between marked lines evenly on white paper and put glass plate onto it to make the surface more even.
Measure 5 times from different locations of the tress The test was done with/without treatment of the tresses with conditioner (1% polymer example 51 in 50/50 glycerine-water; dosage 0.2 gram/gram of hair). The conditioner was also compared with a commercial conditioner L'OREAL Elvive™ color vive after 3, 5, 9 and 15 shampoo washes. The shampoo used was 12 wt % SLES, 2 wt % CAPB.
The test results are given in Table 14:

TABLE 14

| Example 11 | ΔE 3 washes | ΔE 5 washes | ΔE 9 washes | ΔE 15 washes |
|---|---|---|---|---|
| 1% 51 | 0.8 | 1.3 | 2.5 | 4.1 |
| L'OREAL Elvive ™ conditioner | 3.6 | 3.8 | 5.1 | 7.1 |
| No conditioner | 2.2 | 3.8 | 5.2 | 7.2 |

From this Table, it was apparent that the example 51 does indeed demonstrate substantial improvement in wash persistence for this color system when compared to a commercial benchmark and a system without conditioner.

Example 12

In another example using the same procedures as above, a single conditioning treatment with polymer solution of example 51 was compared with a regular treatment with the conditioner (solution 1% of 51 in water-glycerine). It was shown in table 15 that using regular treatment (every shampoo wash treated with the polymer solution prior to shampoo washing) that the red a color (a value) remained constant over the 10-15 washes.

TABLE 15

| Example 12 | a-value 3 washes | a-value 5 washes | a-value 9 washes | a-value 15 washes |
|---|---|---|---|---|
| 1% 51 treatment once | 12.5 | 12.0 | 11.5 | 11.0 |
| 1% 51 treatment before every shampoo wash | 13.1 | 13.1 | 13.1 | 12.5 |

The results clearly demonstrate that with multiple treatments of polymer solution (example 51 polymer), the color fading and color strength improved thru the 15 washes.

Example 13

A cationically modified hydroxyethyl cellulose with following composition was dissolved at 1 wt % in water/propyleneglycol (50/50):

The cationically modified hydroxyethyl cellulose polymer had a HE-MS of approximately 4 and was cationically modified with hydroxypropyltrimonium chloride to a cationic degree of substation of cat-DS 0.33. The cationically modified hydroxyethyl cellulose also had a hydropobic modification of C12 hydrophobe at 3.7 wt %.

Figure 2:
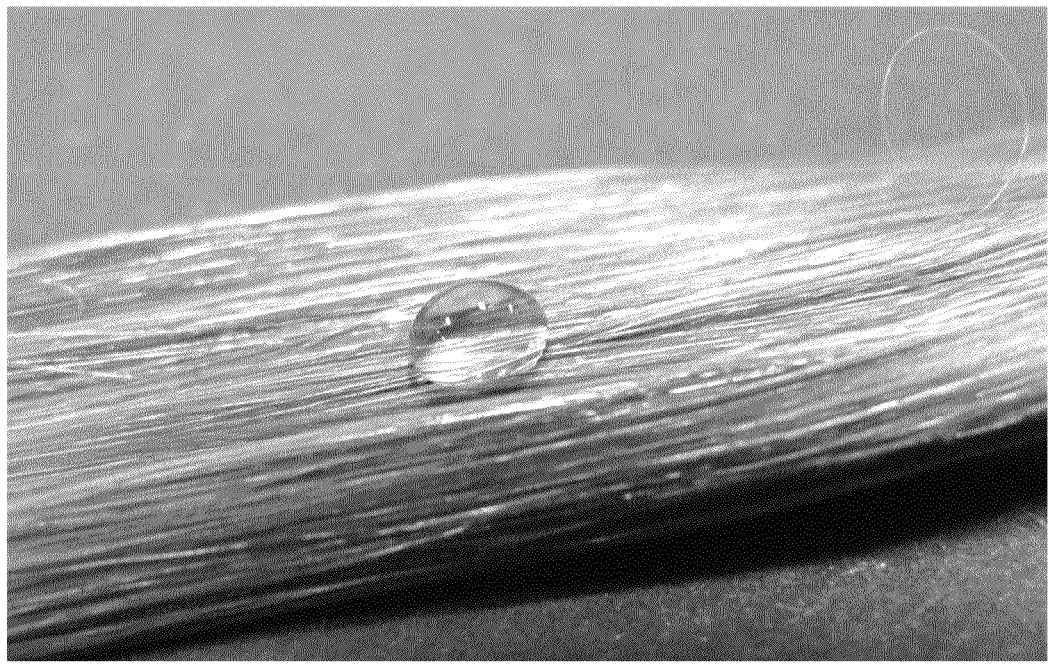
FIG. 2 is a photograph of a water droplet on the surface of a bleached Caucasian hair tress treated with the personal care composition additive of the present invention after thirty (30) minutes demonstrating the hydrophobicity imparted to the hair tress by the personal care composition additive.

The 1 wt % polymer solution of example 13 was applied on bleached Caucasian hair at 0.05 g/gram hair and 0.2 g/g hair resp. and was allowed to dry for twenty four (24) hours. Then the treated hair tress was tested for hydrophobicity by applying a water droplet onto the hair. FIGS. 1 and 2 are photographs of a water droplet on the surface of the hair tress treated with the polymer solution of example 13. From FIGS. 1 and 2, it can be clearly seen that the treated hair tress was quite hydrophobic in nature as the water droplet on the surface of the tress exhibited a high contact angle.

The water droplet was observed to remain on the hair for more than 30 minutes. This droplet behaviour is evidence of the hydrophobicity of the treated tresses.

Figure 3:
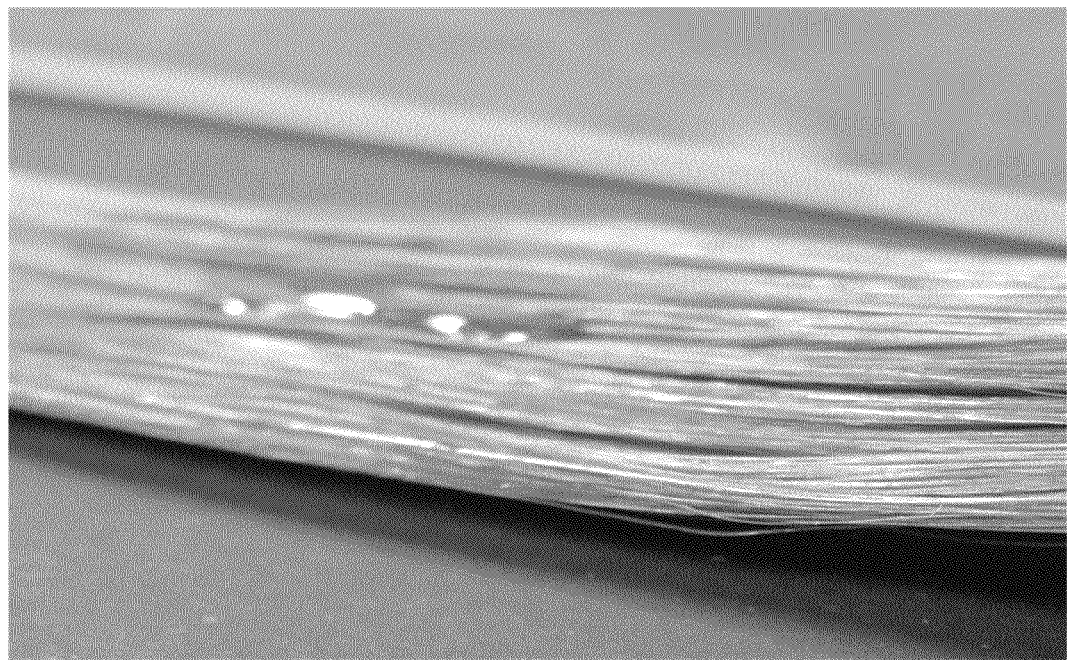
FIG. 3 is a photograph of a water droplet on the surface of a bleached Caucasian hair tress treated with a 5% solution of amodimethicone.
Figure 4:
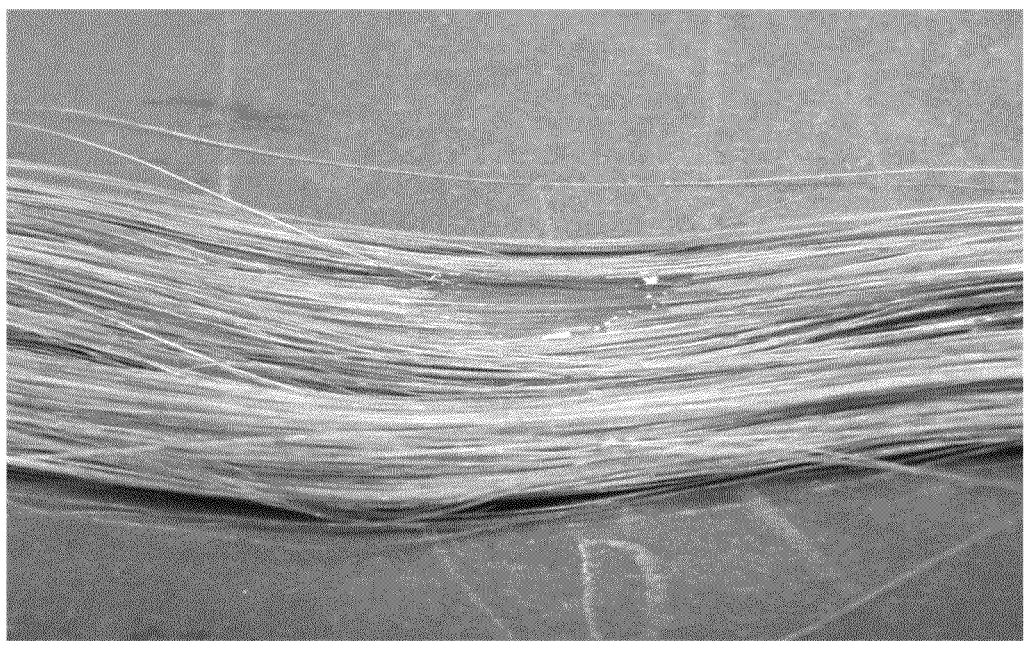
FIG. 4 is a photograph of a water droplet on the surface of a bleached Caucasian hair tress treated with a commercially available conditioner.

FIGS. 3 and 4 are photographs of water droplets applied to bleached Caucasian hair treated with a commercial conditioner and 5 wt % amodimethicone. From FIGS. 3 and 4, it can be clearly seen that the hair tresses treated with a commercial conditioner or amodimethicone do not impart the same degree of hydrophobicity as was observed in the treated hair tress of FIGS. 1 and 2. In the hair tresses treated with a commercial conditioner or amodimethicone, the water droplets exhibited low contact angles with the hair tress surface and were absorbed or at least immediately spread over the tress after applying the water droplet.

Example 14

The polymer of example 7a was used by 1 wt % active in conjunction with cetearyl alcohol at 3 wt % and with a cationic surfactant at 0.75 wt % with water added to 100%. The simple conditioner formula was then applied to hair at 0.05 g/g bleached Caucasian hair and after drying washed 5x with a clarifying shampoo base (12 wt % SLE$_2$S, 2 wt % CAPB) and after the fifth time the hair tress was evaluated for retained hydrophobicity.

Figure 5:
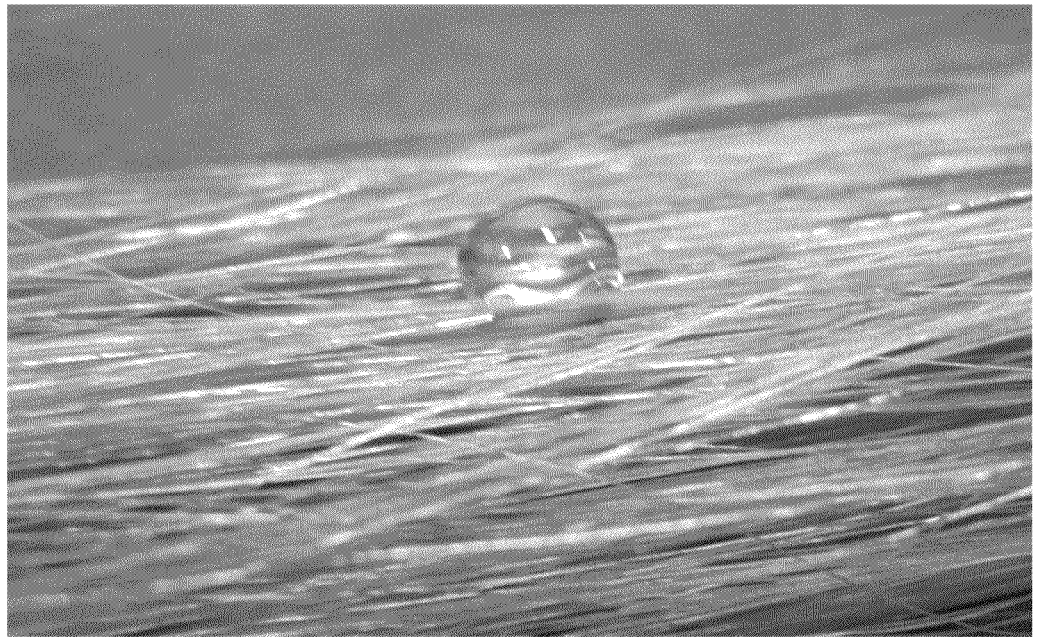
FIG. 5 is a is a photograph of a water droplet on the surface of a bleached Caucasian hair tress treated the personal care composition additive of the present invention comprising a polymer of example 7a as a 1 wt % active in conjunction with cetearyl alcohol at 3 wt % and with a cationic surfactant at 0.75 wt % with the balance being water.

FIG. 5 is a photograph of a water droplet on the hair tress. FIG. 5 clearly demonstrated that the polymer of example 7a provided the treated hair tress with long lasting hydrophobicity after 5 washes with shampoo.

While the invention has been described with respect to specific embodiments, it should be understood that the invention should not be limited thereto and that many variations and modifications are possible without departing from the spirit and scope of the invention.

We claim:

1. A personal care composition additive for providing prolonged benefit to a keratin surface, comprising:
   a) a regular hydrophobically modified cellulose derivative containing cationic monomers having a cationic degree of substitution greater than 0.001 wherein the regular hydrophobically modified cellulose derivative is selected from the group consisting of cetyl modified cellulose derivative, lauryl modified cellulose derivative and butyl modified cellulose derivative, wherein the regular hydrophobically modified cellulose derivative having molecular weight in a range of greater than 50,000 Daltons to less than or equal to 800,000 Daltons, and b) a water miscible, polar solvent,
wherein the concentration of the regular hydrophobically modified cellulose derivative containing cationic monomers is in a range of from about 0.1 wt % to about 20 wt %.

2. The personal care composition additive of claim 1, wherein the regular hydrophobically modified cellulose derivative is regular hydrophobically modified hydroxyethyl cellulose.

3. The personal care composition additive of claim 1, wherein the substantive polymer regular hydrophobically modified cellulose derivative containing cationic monomers has a cationic degree of substitution in a range of from about 0.001 to about 3.0.

4. The personal care composition additive of claim 3, wherein the regular hydrophobically modified cellulose derivative containing cationic monomers has a cationic degree of substitution in a range of from about 0.2 to about 3.0.

5. The personal care composition additive of claim 4, wherein the regular hydrophobically modified cellulose derivative containing cationic monomers has a cationic degree of substitution in a range of from about 0.4 to about 3.0.

6. The personal care composition additive of claim 1, wherein the water miscible, polar solvent is selected from the group consisting of alcohols, polyols, and glycol ethers.

7. The personal care composition additive of claim 6, wherein the water miscible, polar solvent is a polyol selected from the group consisting of cyclitol, diols, glycerol, Balsaminol B, butanetriol, balsaminapentaol, cucurbalsaminol, and propylene glycol.

8. The personal care composition additive of claim 6, wherein the glycol ether is selected from the group consisting of diethylene glycol dimethyl ether, diethylene glycol monobutyl ether acetate, diethylene glycol monobutyl ether, diethylene glycol monoethyl ether acetate, diethylene glycol monoethyl ether, diethylene glycol monohexyl ether, diethylene glycol monomethyl ether acetate, diethylene glycol monomethyl ether, ethylene glycol dibutyl ether, ethylene glycol diethyl ether, ethylene glycol dimethyl ether, ethylene glycol monoacetate, ethylene glycol monobutyl ether acetate, ethylene glycol monoethyl ether acetate, ethylene glycol monoethyl ether, ethylene glycol monohexyl ether, ethylene glycol monomethyl ether acetate, ethylene glycol monomethyl ether, ethylene glycol monooctyl ether, ethylene glycol monophenyl ether, ethylene glycol monopropyl ether, triethylene glycol, triethylene glycol dimethyl ether, triethylene glycol monoethyl ether, and triethylene glycol monomethyl ether.

9. The personal care composition additive of claim 1, wherein the water miscible, polar solvent is in a mixture with water.

10. The personal care composition additive of claim 9, wherein the water miscible, polar solvent is in a mixture in the range of about 10:90 to about 90:10 by weight with water.

11. The personal care composition additive of claim 10, wherein the water miscible, polar solvent is in a mixture in the range of about 25:75 to about 75:25 by weight with water.

12. The personal care composition additive of claim 11, wherein the water miscible, polar solvent is in a mixture of about 50:50 by weight with water.

13. The personal care composition additive of claim 1, wherein the concentration of the regular hydrophobically modified cellulose derivative in the water miscible, polar solvent is about 1.0 wt %.

14. The personal care composition additive of claim 12, wherein the water miscible, polar solvent is glycerine and wherein the regular hydrophobically modified cellulose derivative is regular hydrophobically modified hydroxyethyl cellulose having a molecular weight of about 300,000 Daltons.

15. A personal care composition comprising:
a) a personal care composition additive for providing prolonged benefit to a keratin surface, comprising (i) a regular hydrophobically modified cellulose derivative containing cationic monomers having a cationic degree of substitution greater than 0.001 wherein the regular hydrophobically modified cellulose derivative is selected from the group consisting of cetyl modified cellulose derivative, lauryl modified cellulose derivative and butyl modified cellulose derivative, wherein the regular hydrophobically modified cellulose derivative having molecular weight in a range of greater than 50,000 Daltons to less than or equal to 800,000 Daltons, and (ii) a water miscible, polar solvent, wherein the concentration of the regular hydrophobically modified cellulose derivative containing cationic monomers in a range of from about 0.1 wt % to about 20 wt %, and
b) a personal care active ingredient.

16. The personal care composition of claim 15, wherein the personal care composition comprises a hair care product.

17. The personal care composition of claim 16, wherein the hair care product comprises a conditioning system.

18. The personal care composition of claim 15, wherein the personal care composition comprises a skin care product.

19. The personal care composition of claim 18, wherein prolonged benefit provided by the personal care composition additive is selected from the group consisting of perfumes, skin coolants, emollients, deodorants, antiperspirant actives, moisturizing agents, sunscreen active ingredients and hair treatment agent.

* * * * *

UNITED STATES PATENT AND TRADEMARK OFFICE
CERTIFICATE OF CORRECTION

| | |
|---|---|
| PATENT NO. | : 8,790,627 B2 |
| APPLICATION NO. | : 13/168390 |
| DATED | : July 29, 2014 |
| INVENTOR(S) | : Paquita Erazo-Majewicz et al. |

It is certified that error appears in the above-identified patent and that said Letters Patent is hereby corrected as shown below:

In the Claims:

At column 15, claim number 3, line number 11, please delete the words "substantive polymer".

Signed and Sealed this
Twenty-first Day of October, 2014

Michelle K. Lee
*Deputy Director of the United States Patent and Trademark Office*